United States Patent
Onishi (10) Patent No.: US 12,257,074 B2
(45) Date of Patent: Mar. 25, 2025

(54) STRESS ESTIMATION DEVICE, STRESS ESTIMATION METHOD, AND RECORDING MEDIA

(71) Applicant: NEC Corporation, Tokyo (JP)

(72) Inventor: Yoshifumi Onishi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 378 days.

(21) Appl. No.: 17/771,876

(22) PCT Filed: Nov. 6, 2019

(86) PCT No.: PCT/JP2019/043491
§ 371 (c)(1),
(2) Date: Apr. 26, 2022

(87) PCT Pub. No.: WO2021/090402
PCT Pub. Date: May 14, 2021

(65) Prior Publication Data
US 2022/0370009 A1 Nov. 24, 2022

(51) Int. Cl.
*A61B 5/00* (2006.01)
(52) U.S. Cl.
CPC ............ *A61B 5/4884* (2013.01); *A61B 5/004* (2013.01)
(58) Field of Classification Search
CPC .............................. A61B 5/4884; A61B 5/004
See application file for complete search history.

(56) References Cited

U.S. PATENT DOCUMENTS

| 2009/0268022 | A1* | 10/2009 | Omi | A61B 5/18 |
| | | | | 348/135 |
| 2017/0071523 | A1* | 3/2017 | Jain | A61B 5/02416 |
| 2017/0368936 | A1 | 12/2017 | Kojima | |
| 2018/0310841 | A1* | 11/2018 | Khwaja | A61B 5/1116 |
| 2019/0227547 | A1* | 7/2019 | Sugahara | B60W 50/0098 |

FOREIGN PATENT DOCUMENTS

| JP | 2001198113 A | * | 7/2001 |
| JP | 2009095387 A | * | 5/2009 |
| JP | 2009-261516 A | | 11/2009 |
| JP | 2011-167323 A | | 9/2011 |
| JP | 2016-107095 A | | 6/2016 |

(Continued)

OTHER PUBLICATIONS

Tsujikawa, Y. Onishi, Y. Kiuchi, T. Ogatsu, A. Nishino, S. Hashimoto, "Drowsiness Estimation from Low-Frame-Ratio Facial Videos using Eyelid Variability Features," Conf Proc IEEE Eng Med Biol Soc. Jul. 2018;2018:5203-5206., 2018. (Year: 2018).*

(Continued)

*Primary Examiner* — Michael J Dalbo
*Assistant Examiner* — Kaleria Knox (57) ABSTRACT

The stress estimation device acquires the awakening degree of the subject and calculates the feature amount of the acquired awakening degree. The feature amount of the awakening degree is, for example, a ratio at which the temporal change of the awakening degree is within a predetermined range, information defining a histogram showing the distribution of the temporal change of the awakening degree, and the like. Then, the stress estimation device estimates the stress from the calculated feature amount using the stress model.

5 Claims, 9 Drawing Sheets

(56) References Cited

FOREIGN PATENT DOCUMENTS

| JP | 2018005343 A | * | 1/2018 | ............. B60K 28/06 |
| WO | WO-2019037045 A1 | * | 2/2019 | ........... A61B 5/0205 |
| WO | WO-2019146123 A1 | * | 8/2019 | |

OTHER PUBLICATIONS

Frans VanderWerf "Eyelid Movements: Behavioral Studies of Blinking in Humans Under Different Stimulus Conditions"; pp. 2784-2796 (Year: 2003).*
International Search Report for PCT Application No. PCT/JP2019/043491, mailed on Feb. 4, 2020.

* cited by examiner

STRESS ESTIMATION DEVICE, STRESS ESTIMATION METHOD, AND RECORDING MEDIA

This application is a National Stage Entry of PCT/JP2019/043491 filed on Nov. 6, 2019, the contents of all of which are incorporated herein by reference, in their entirety.

TECHNICAL FIELD

The present invention relates to a technique for estimating stress.

BACKGROUND ART

The modern society is said to be a stressful society, and people are under stress in various environments such as the workplace and home. Therefore, there have been proposed various techniques for judging and estimating human stress. For example, Patent Document 1 proposes a method for determining the degree of stress during sleep by detecting body movement, respiration, pulse waves, and the like during sleep of a subject. Patent Document 2 proposes a method for estimating a stress state of a subject from human body information by detecting the human body information such as face image data and voice data of the subject using a camera or a microphone and associating the human body information with the stress amount detected by a sensor or the like in advance.

PRECEDING TECHNICAL DOCUMENTS

Patent Document

Patent Document 1: Japanese Patent Application Laid-open under No. 2016-107095
Patent Document 2: Japanese Patent Application Laid-open under No. 2011-167323

SUMMARY

Problem to be Solved by the Invention

It is known that the stress felt by workers during work in the workplace leads to lowering of efficiency and safety of work, and also affects the health of workers. Therefore, it is required to monitor the stress of workers from the viewpoint of improvement of work efficiency and health management of workers.

One of the objects of the present invention is to quantitatively estimate stress without imposing a burden on a subject.

Means for Solving the Problem

To solve the above problems, in one aspect of the present invention, the stress estimation device comprises:
an awakening degree acquisition unit configured to acquire an awakening degree of a subject;
a feature amount calculation unit configured to calculate a feature amount of the acquired awakening degree; and
a stress estimation unit configured to estimate stress from the calculated feature amount using a stress model.

In another aspect of the present invention, a stress estimation method comprises:
acquiring an awakening degree of a subject;
calculating a feature amount of the acquired awakening degree; and
estimating stress from the calculated feature amount using a stress model.

In still another aspect of the present invention, the recording medium records a program, the program causing a computer to execute:
acquiring an awakening degree of a subject;
calculating a feature amount of the acquired awakening degree; and
estimating stress from the calculated feature amount using a stress model.

Effect of the Invention

According to the present invention, it becomes possible to quantitatively estimate stress without imposing a burden on a subject.

EXAMPLE EMBODIMENTS

Hereinafter, preferred example embodiments of the present invention will be described with reference to the accompanying drawings.

First Example Embodiment (Configuration)

Figure 1:
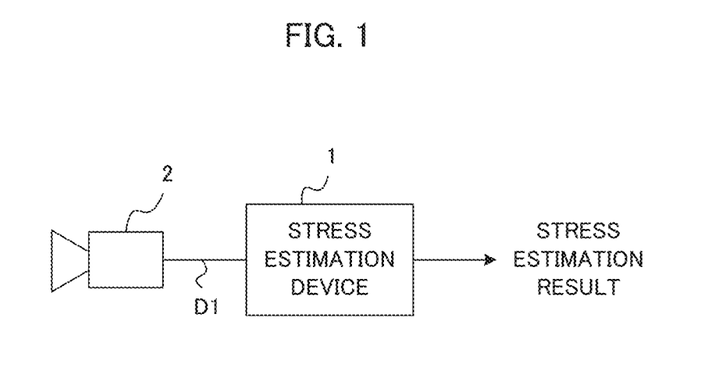
FIG. 1 shows a schematic configuration of a stress estimation device according to a first example embodiment of the present invention.

FIG. 1 shows a schematic configuration of a stress estimation device according to a first example embodiment of the present invention. The stress estimation device 1 is connected to a camera 2. The camera 2 captures image of the face of the subject of the stress estimation (hereinafter simply referred to as the "subject") and transmits the captured image D1 to the stress estimation device 1. Typically, the camera 2 may be a so-called webcam, infrared camera or the like, provided on a PC (Personal Computer) used by the subject at the desk work. However, the example of the camera 2 is not limited thereto, and a device that is provided on the glasses or the like worn by the subject and detects the movement (opening and closing) of the subject's eyelid by measuring the eye potential may be used, for example.

The stress estimation device 1 estimates the stress of the subject by analyzing the captured image D1, and outputs the stress estimation result. The stress estimation result is supplied to various devices that utilize it. For example, in a system that manages the work and health of employees, the stress estimation results of the employees can be monitored by a server. When it is judged that the stress of a certain employee is high, a message prompting the employee to take a rest may be displayed on the display of the PC that the employee is using.

Figure 2:
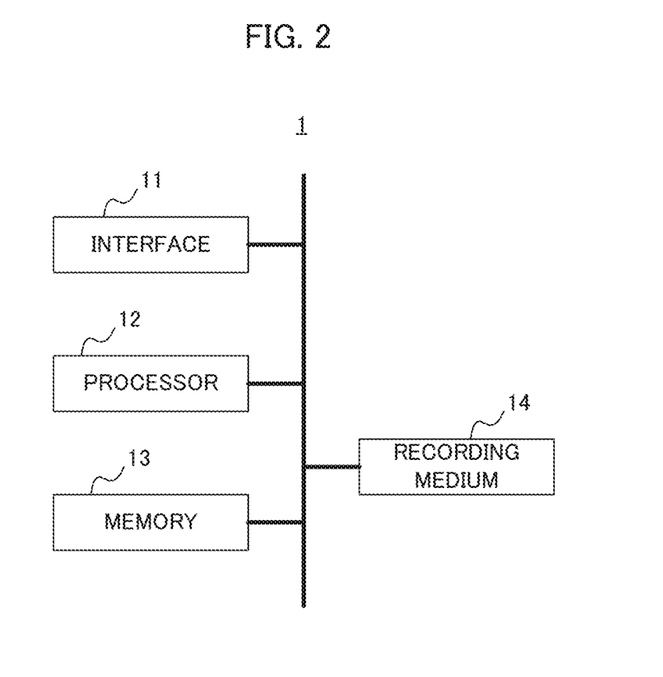
FIG. 2 shows a hardware configuration of the stress estimation device according to the first example embodiment.

FIG. 2 is a block diagram showing a hardware configuration of the stress estimation device 1. As illustrated, the stress estimation device 1 includes an interface 11, a processor 12, a memory 13, and a recording medium 14.

The interface 11 exchanges data with the camera 2. The interface 11 is used to receive the captured image generated by the camera 2. The interface 11 is also used when the stress estimation device 1 outputs the stress estimation result to the device utilizing the stress estimation result.

The processor 12 is a computer such as a CPU (Central Processing Unit) and controls the entire stress estimation device 1 by executing a program prepared in advance. The memory 13 is configured by a ROM (Read Only Memory), RAM (Random Access Memory), or the like. The memory 13 stores various programs to be executed by the processor 12. The memory 13 is also used as a work memory during the execution of various processes by the processor 12.

The recording medium 14 is a non-volatile and non-transitory recording medium such as a disk-shaped recording medium or a semiconductor memory, and is configured to be detachable from the stress estimation device 1. The recording medium 14 records various programs to be executed by the processor 12. When the stress estimation device 1 performs the stress estimation process, a program recorded on the recording medium 14 is loaded into the memory 13 and executed by the processor 12.

Figure 3:
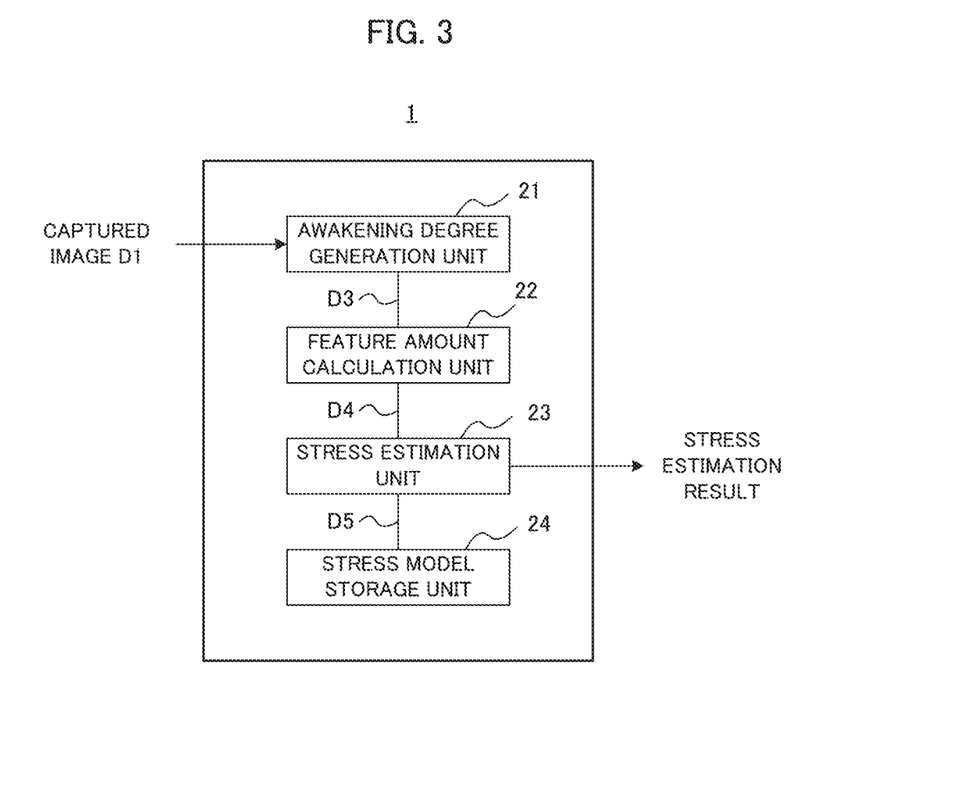
FIG. 3 shows a functional configuration of the stress estimation device according to the first example embodiment.

FIG. 3 is a block diagram showing a functional configuration of the stress estimation device 1. The stress estimation device 1 functionally includes an awakening degree generation unit 21, a feature amount calculation unit 22, a stress estimation unit 23, and a stress model storage unit 24. Incidentally, the awakening degree generation unit 21, the feature amount calculation unit 22, and the stress estimation unit 23 are realized by the processor 12 executing the program, and the stress model storage unit 24 is realized by the memory 13.

The awakening degree generation unit 21 generates the awakening degree D3 from the captured image D1 supplied from the camera 2. The awakening degree is a value that indicates the degree that a person is awake. A condition of high awakening degree is a condition in which a person is wide-awake, and a condition of low awakening degree is a condition in which a person is sleepy. The awakening degree generation unit 21 analyzes the captured image D1 of the subject's face, calculates the awakening degree D3 of the subject, and supplies it to the feature amount calculation unit 22.

Figure 4:
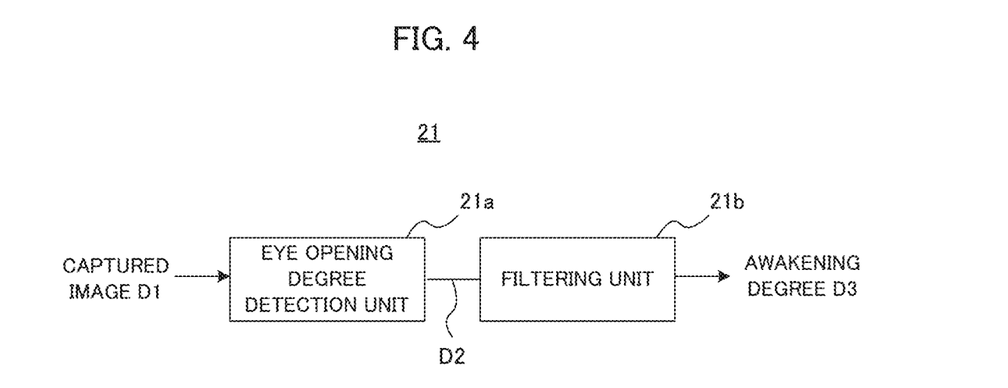
FIG. 4 is an example of a configuration of an awakening degree generation unit.

FIG. 4 is a block diagram showing a configuration example of the awakening degree generation unit 21. In this example, the awakening degree generation unit 21 includes an eye opening degree detection unit 21a and a filtering unit 21b. The eye opening degree detection unit 21a detects the eye opening degree of the subject by the image processing of the captured image D1, and outputs the time series signal D2 of the eye opening degree to the filtering unit 21b. The "eye opening degree" is a value indicating the opening degree of the subject's eye, and is calculated by the analysis of the captured image D1. As the eye opening degree, an eye opening degree of one of the right eye and the left eye of the subject may be used, or an average value of the eye opening degrees of the left eye and the right eye may be used.

The filtering unit 21b performs filtering to remove the variation component of the signal caused by the blink of the subject from the time series signal D2 of the eye opening degree. Generally, since the time of human blinking is about 0.1 to 0.15 seconds, its frequency is about 10 to 6.7 Hz. Therefore, the filtering unit 21b outputs a signal obtained by removing the signal component of the above frequency band from the time series signal D2 of the eye opening degree as the awakening degree D3. Thus, the awakening degree becomes a time series signal indicating the opening and closing of the eyes other than the blinking among the eye opening degree of the human eye. In other words, the awakening degree is not due to the blinking, which is a physiological phenomenon, but rather is a value obtained by quantifying the state in which the subject's eye opens and closes due to sleepiness. While the awakening degree is generated using an eye opening degree of the subject in the captured image in the example of FIG. 4, the awakening degree generation unit 21 may generate an awakening degree by a method other than this.

For example, the awakening degree generation unit 21 may generate an awakening degree using a technique described in the following document.

Tsujikawa, Y. Onishi, Y. Kiuchi, T. Ogatsu, A. Nishino, S. Hashimoto, "Drowsiness Estimation from Low-Frame-Ratio Facial Videos using Eyelid Variability Features," Conf Proc IEEE Eng Med Biol Soc. 2018 July; 2018:5203-5206, 2018.

The feature amount calculation unit 22 calculates a ratio at which the temporal change of the awakening degree D3, which is a time series signal, becomes within a predetermined range as the feature amount D4. Specifically, the feature amount calculation unit 22 calculates the first-order differential or the second-order differential of the awakening degree D3 supplied from the awakening degree generation unit 21 as the temporal change, and supplies a ratio at which the value becomes smaller than a predetermined threshold value to the stress estimation unit 23 as the feature amount D4. Incidentally, the reason for using such a value as the feature amount will be described later.

The stress estimation unit 23 estimates the stress from the feature amount using the stress model. The stress model is a learned model of stress generated in advance by machine learning. For example, the feature amount obtained from the awakening degree is used as training data, and the stress value at that time obtained by questionnaire or else is used as a label to learn the model in advance. Thereby, the stress model is generated. Incidentally, when the stress value is treated as a continuous value, the stress model becomes a regression model, and a support vector regression (SCR: Support Vector Regression) or a neural network of deep learning can be used, for example. When the stress values are discrete classes, the stress model becomes a classification model, and a support vector machine (SVM: Support Vector Machine) or a neural network can be used.

Information of the stress model (hereinafter also referred to as "stress model information") D5 is stored in advance in the stress model storage unit 24. When the stress estimation unit 23 acquires the feature amount D4 based on the awakening degree in the situation of performing the stress estimation, the stress estimation unit 23 estimates the stress from the feature amount D4 using the stress model and outputs the stress as the stress estimation result.

(Feature Amount)

Next, the feature amount calculated by the feature amount calculation unit 22 will be described in detail. As described above, since the feature amount is a value used as an input when the stress is estimated using a stress model, the feature amount needs to be a value that is correlated with the level and/or the amount of the stress. Therefore, as candidates of the feature amount, among the values based on the awakening degree, the followings are examined: (a) an average awakening degree, (b) a ratio at which the awakening degree is smaller than a threshold, (c) a ratio at which the first-order differential of the awakening degree is smaller than a threshold, and (d) a ratio at which the second-order differential of the awakening degree is smaller than a threshold.

Figure 5A:
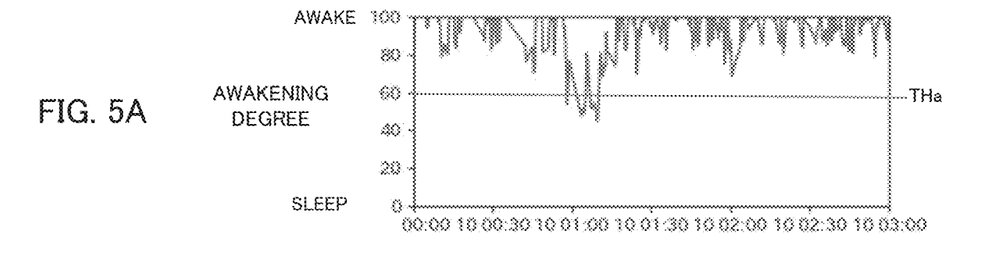
FIGS. 5A to 5C are graphs each showing an example of the awakening degree.

FIG. 5A is a graph showing an example of a time series signal of the awakening degree generated by the awakening degree generation unit 21. In the graph of FIG. 5A, the horizontal axis indicates the time, and the vertical axis indicates the value of the awakening degree. The example of FIG. 5A shows the variation of the awakening degree in three hours from a certain measurement start time (supposed to be "00:00"). In this example, the awakening degree is a discrete value (digital value) of a predetermined time interval (for example, about 10 seconds), and takes a value of "0 to 100". The awakening degree "100" indicates an awake state, and the awakening degree "0" indicates a sleeping state. The larger the value of the awakening degree is, the more awake the subject is. The smaller the value of the awakening degree is, the sleepier the subject is.

Figure 5B:
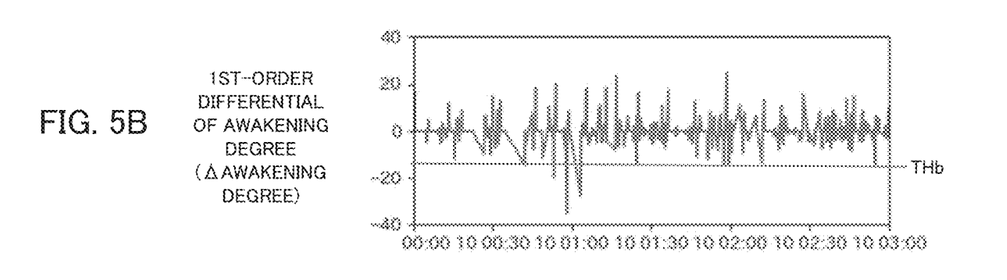

FIG. 5B is a graph showing the first-order differential of the awakening degree. In this example, the awakening degree is a discrete value, and the first-order differential is a difference value. In the graph of FIG. 5B, the horizontal axis indicates the elapsed time from the measurement start time, and the vertical axis indicates the first-order differential of the awakening degree (also referred to as "$\Delta$ awakening degree"). The $\Delta$ awakening degree indicates variation of the awakening degree of the subject, i.e., the variation of sleepiness of the subject. When $\Delta$ awakening degree is near "0", the variation of sleepiness of the subject is small. When the positive and negative values, i.e., the absolute value of $\Delta$ awakening degree increase, the variation of sleepiness of the subject increases. In addition, a condition in which variation of sleepiness is large is a state in which sleepiness and awakening are repeated.

Figure 5C:
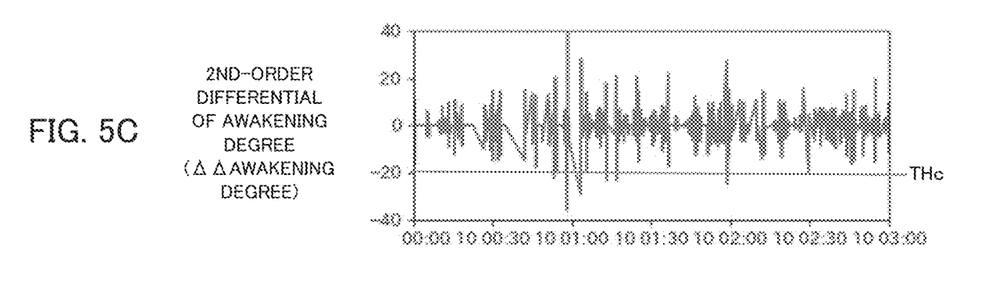

FIG. 5C is a graph showing the second-order differential of the awakening degree. In the graph of FIG. 5C, the horizontal axis indicates the elapsed time from the measurement start time, and the vertical axis indicates the second-order differential of the awakening degree (also referred to as "$\Delta\Delta$ awakening degree"). The $\Delta\Delta$ awakening degree is a value which shows rapid variation of awakening degree of the subject, i.e., rapid variation of the subject's sleepiness. When the $\Delta\Delta$ awakening degree is near "0", rapid variation of sleepiness of the subject is small. When the positive and negative values, i.e., the absolute value of the $\Delta\Delta$ awakening degree increase, rapid variation of sleepiness of the subject increases.

Now, it is generally said that the greater the sleepiness, the greater the stress is in the daytime and during work. According to this idea, for example, if a certain appropriate threshold THa is set as shown in FIG. 5A, when the awakening degree is equal to or smaller than the threshold THa, it is possible to estimate that the subject is in a sleepy state, i.e., in a state of high stress. Therefore, we first examined the relation of the human stress with (a) the average awakening degree and (b) the ratio at which the awakening degree becomes equal to or smaller than the threshold THa.

Figure 6A:
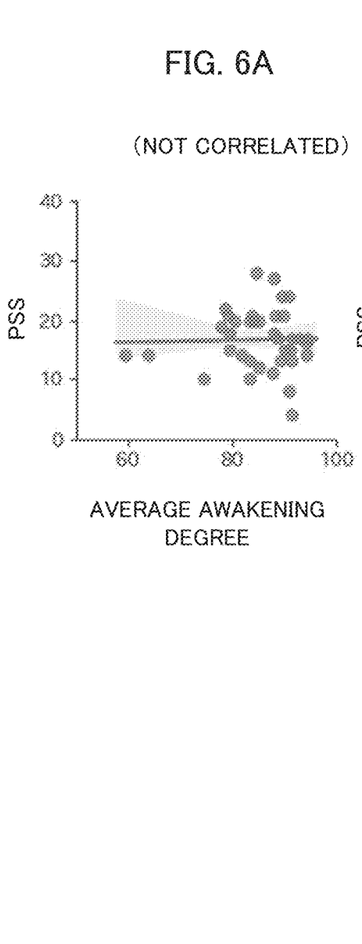
FIGS. 6A to 6D are graphs each showing a correlation between a value based on the awakening degree and stress.

FIG. 6A is a graph showing the relation between the average awakening degree and PSS (Perceived Stress Scale). Incidentally, PSS is the stress value calculated based on the questionnaire results. In FIG. 6A, the vertical axis indicates the PSS and takes a value of "0 to 40". In this example, "40" is the maximum value of the PSS, which corresponds to the state of maximum stress. The horizontal axis indicates the average awakening degree, i.e., the average value of the awakening degree. In this example, the awakening degree was calculated by capturing the face image of the subject in the workplace environment over a predetermined period (1 month), and the average awakening degree was calculated. Also, the questionnaire was carried out after the lapse of the predetermined period, and the PSS was calculated based on the questionnaire result. In FIG. 6A, each point shows the relationship between the average value and the PSS of one subject. The straight line in the figure is a regression line calculated based on the data of the subjects, and the gray area in the figure indicates the confidence interval of the regression line. The graph in FIG. 6A shows that there is little correlation between the average awakening degree and the PSS, and the average awakening degree is not appropriate as a feature amount.

Figure 6B:
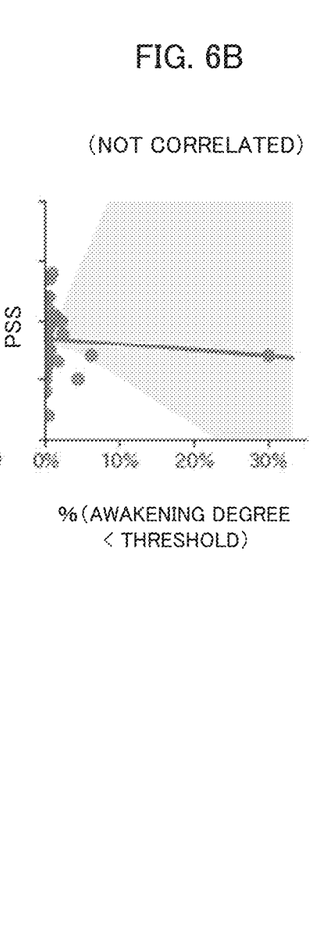

FIG. 6B shows the relationship between the ratio at which the awakening degree becomes smaller than a certain threshold (referred to as "% (awakening degree<threshold)") and the PSS. Specifically, % (awakening degree<threshold) is calculated as follows.

$$\%(\text{awakening degree}<\text{threshold})=(\text{total time in which the awakening degree is smaller than the threshold})/(\text{predetermined period}) \quad (1)$$

Incidentally, the threshold value is determined in advance to be an appropriate value as the threshold value THa in FIG. 5A, for example. From the graph of FIG. 6B, it can be seen that there is little correlation between the ratio at which the awakening degree becomes smaller than the threshold value and the PSS, and that the ratio at which the awakening degree becomes smaller than the threshold value is not appropriate as a feature amount.

Figure 6C:
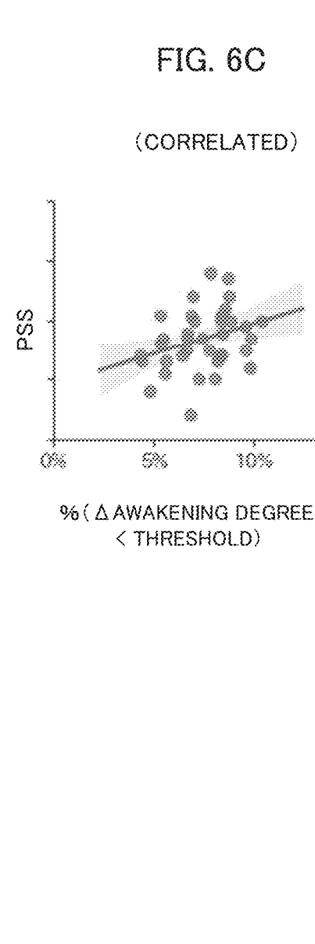

Next, the relationship between the PSS and the value based on the first-order differential or second-order differential of the awakening degree is examined. FIG. 6C shows the relationship between the ratio at which the first-order differential of the awakening degree ($\Delta$ awakening degree) becomes smaller than the threshold ("% ($\Delta$ awakening degree<threshold)") and the PSS. Specifically, % ($\Delta$ awakening degree<threshold) is calculated as follows.

$$\%(\Delta\text{awakening degree}<\text{threshold})=(\text{total time in which }\Delta\text{awakening degree is smaller than threshold})/(\text{predetermined period}) \quad (2)$$

Incidentally, the threshold is determined in advance to be an appropriate value as the threshold THb in FIG. 5B. The graph in FIG. 6C shows that there is a correlation between the first-order differential of the awakening degree and the PSS. Therefore, % ($\Delta$ awakening degree<threshold) is considered appropriate as a feature amount.

Figure 6D:
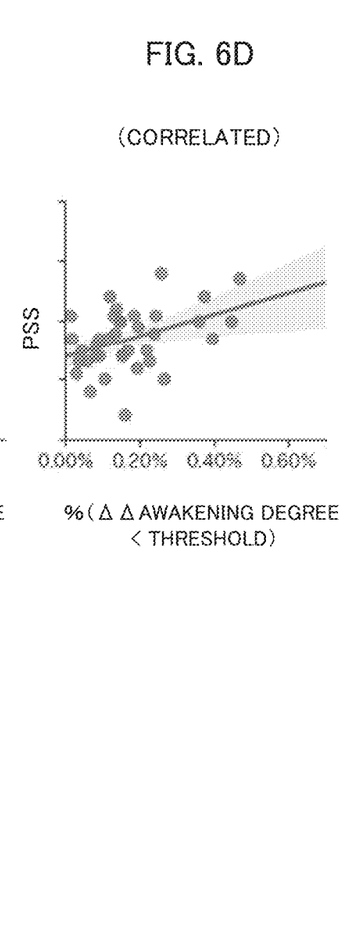

FIG. 6D shows the relationship between the ratio at which the second-order differential of the awakening degree ($\Delta\Delta$ awakening degree) becomes smaller than the threshold ("% ($\Delta\Delta$ awakening degree<threshold)") and the PSS. Specifically, % ($\Delta\Delta$ awakening degree<threshold) is calculated as follows.

%(ΔΔawakening degree<threshold)=(total time in which ΔΔawakening degree is smaller than the threshold)/(predetermined period)     (3)

Incidentally, the threshold value is determined in advance to be an appropriate value as the threshold THc in FIG. 5C. The graph in FIG. 6D shows that there is a correlation between the second-order differential of awakening degree and the PSS. Therefore, % (ΔΔ awakening degree<threshold) is considered appropriate as a feature amount.

Figure 7A:
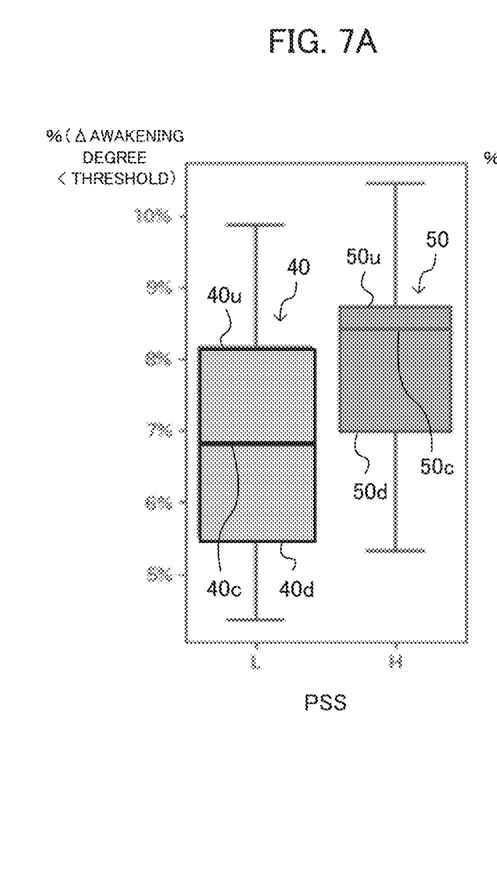
FIGS. 7A and 7B are graphs each showing a relationship between the value based on the awakening degree and a level of stress.

FIG. 7A shows the relationship between the level of stress and % (Δ awakening degree<threshold) when the PSS is divided into two classes, i.e., the high stress (H) class and the low (L) stress class using a certain threshold value. In FIG. 7A, the vertical axis shows % (Δ awakening degree<threshold), and the horizontal axis shows the level of the stress (H/L). In FIG. 7A, the rectangle 40 shows the distribution of the subjects with low stress, and the rectangle 50 shows the distribution of the subjects with high stress. In the graph of stress "L" in FIG. 7A, the lower end 40d of the rectangle 40 indicates the position corresponding to the number of the subjects which is ¼ of the total number of the subjects counted from the smallest value of % (Δ awakening degree<threshold) in the distribution of the subjects. The upper end 40u of the rectangle 40 indicates a position corresponding to the number of the subjects which is ¼ of the total number of the subjects counted from the largest value of % (Δ awakening degree<threshold) in the distribution of subjects. The line segment 40c in the rectangle 40 indicates the position corresponding to the median value of the value of % (Δ awakening degree<threshold) in the distribution of the subjects. For the rectangle 50 in the graph of stress "H" in FIG. 7A, the meaning of the lower end 50d, the upper end 50u, and the line segment 50c are the same.

Figure 7B:
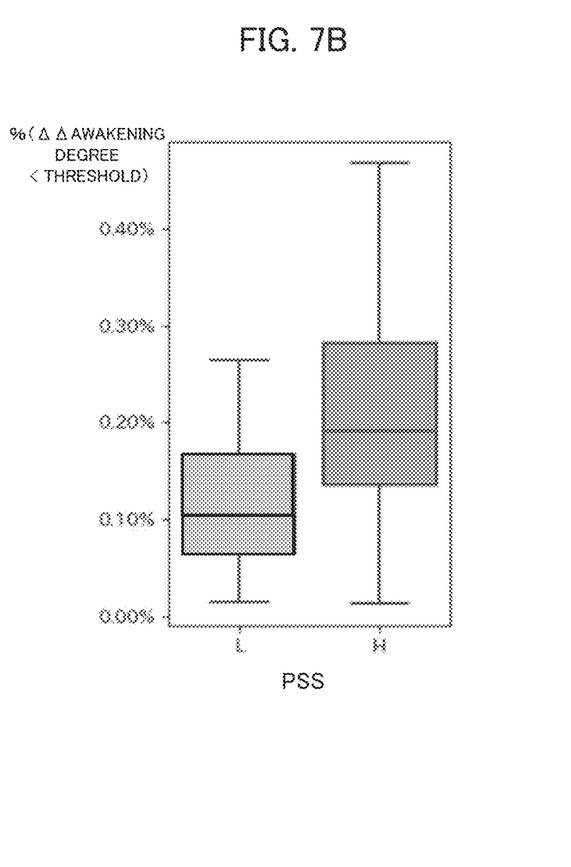

In addition, FIG. 7B shows the relationship between the level (H/L) of stress and % (ΔΔ awakening degree<threshold) when the PSS is divided into two classes, i.e., the high (H) stress class and the low (L) stress class using a certain threshold value. In FIG. 7B, the vertical axis indicates % (ΔΔ awakening degree<threshold), and the horizontal axis indicates the level of the stress. In FIG. 7B, the rectangle drawn on the two graphs shows the distribution of the number of the subjects as in FIG. 7A. The meaning of the upper end, the lower end, and the line segment of each rectangle is also the same as in FIG. 7A.

As shown in FIGS. 7A and 7B, it can be seen that when either % (Δawakening degree<threshold value) or % (ΔΔ awakening degree<threshold value) is used, the subjects with high stress and the subjects with low stress have different distributions. Actually, when the statistical significance probability (p-value) is calculated, the p-value of the ratio "% (Δ awakening degree<threshold)" at which the first-order differential of the awakening degree becomes smaller than the threshold value is "0.03", and the p-value of the ratio "% (ΔΔawakening degree<threshold)" at which the second-order differential of the awakening degree becomes smaller than the threshold value is "0.019". Since both values are smaller than the general reference value "0.05", the classification results using "% (Δ awakening degree<threshold value)" and "% (ΔΔ awakening degree<threshold value)" are recognized to have significant differences. In particular, since the p-value (0.019) of "% (ΔΔ awakening degree<threshold)" is smaller than the p-value (0.03) of "% (Δ awakening degree<threshold)," the ratio at which the second-order differential of the awakening degree is smaller than the threshold is considered more suitable for classification of stress.

Thus, it can be seen that the ratio at which the simple average awakening degree or the awakening degree becomes smaller than the threshold value is not correlated with the stress value and is not effective as a feature amount used for stress estimation. On the other hand, it can be seen that the ratio based on the first-order differential or the second-order differential of the awakening degree is highly correlated with the stress value, and is effective as a feature amount used for stress estimation. Therefore, in the present example embodiment, the ratio at which the temporal change of the awakening degree becomes within a predetermined range, specifically, the ratio at which the first-order differential or the second-order differential of the awakening degree becomes smaller than the threshold value is used as the feature amount.

(Stress Estimation Process)

Figure 8:
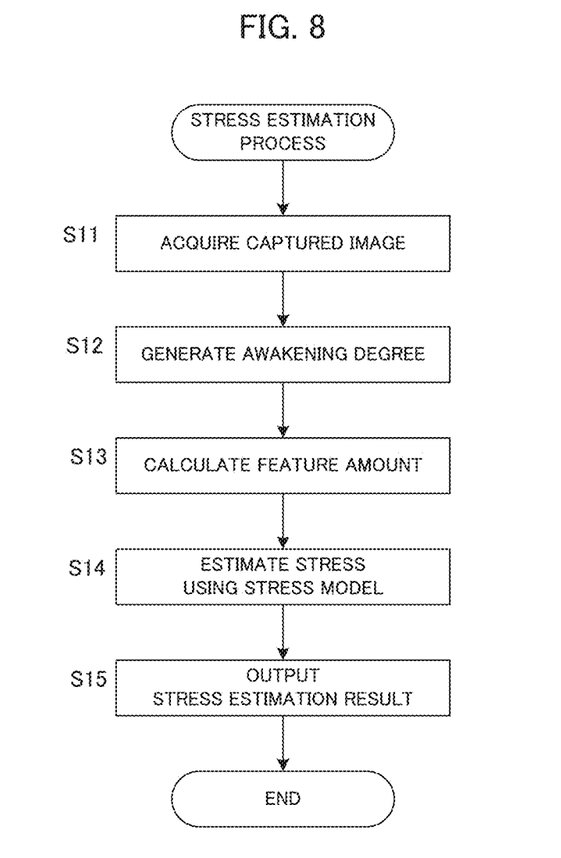
FIG. 8 is a flowchart of a stress estimation process.

Next, the stress estimation process performed by the stress estimation device 1 will be described. FIG. 8 is a flowchart of the stress estimation process. This process is implemented by the processor 12 shown in FIG. 1 executing a program prepared in advance and functioning as each element shown in FIG. 3.

First, the awakening degree generation unit 21 acquires the captured image D1 from the camera 2 (Step S11), and calculates the awakening degree D3 (Step S12). Next, the feature amount calculation unit 22 calculates the feature amount D4 from the awakening degree D3 (Step S13). As the feature amount D4, as described above, the ratio at which the temporal change of the awakening degree becomes within a predetermined range, specifically, the ratio at which the first-order differential or the second-order differential of the awakening degree becomes smaller than the threshold value is calculated.

Next, the stress estimation unit 23 acquires the stress model information D5 stored in the stress model storage unit 24 and inputs the feature amount D4 to the stress model to estimate the stress (Step S14). Then, the stress estimation unit 23 outputs the stress estimation result to an external device or the like (step S15). Thus, the stress estimation process is completed.

(Evaluation Example of Stress Estimation Results)

Figure 9:
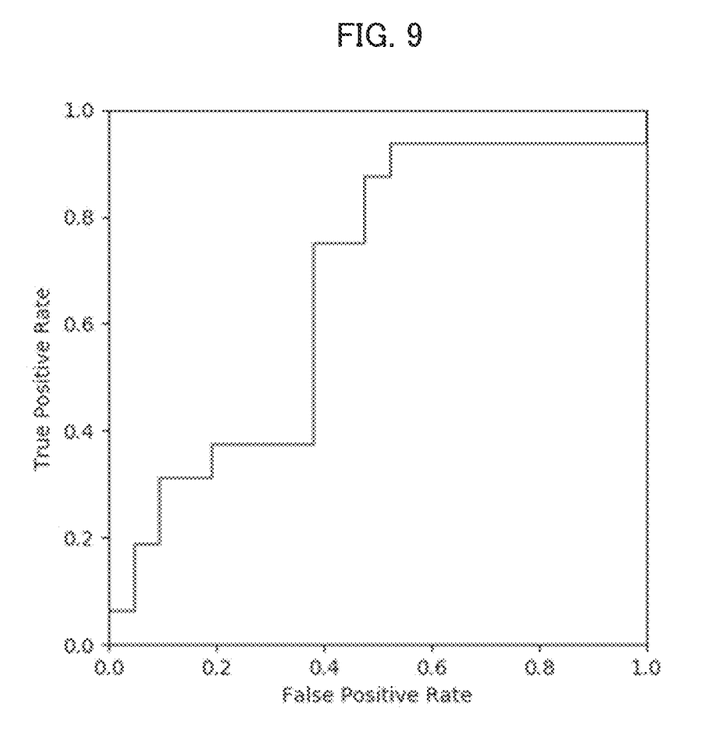
FIG. 9 is a graph showing an evaluation result of stress estimation.

Next, an example of evaluation of the above stress estimation results will be described. The PSS was divided into two classes of high and low (L/H), and the above stress estimation was carried out using the stress model which is a two-class classification model. There were data of 37 persons as subjects, in which 21 persons were "L" in stress, 16 persons were "H" in stress, and the chance level was 0.56. As the feature amount, "% (ΔΔ awakening degree<threshold)" was used. Among the 37 persons, learning of the stress model is performed with the data of 36 persons, and the evaluation of the model was performed using the data of the remaining 1 person. FIG. 9 shows the ROC (Receiver Operating Characteristic Curver) curve obtained as the evaluation result. In this ROC curve, AUC (Area under an ROC curve) were calculated as "0.67", and it was proven that appropriate classification performance was obtained. As described above, in the present example embodiment, since the stress is estimated based on the awakening degree of the subject, it is possible to estimate the stress without imposing a burden on the subject.

Second Example Embodiment

Next, a second example embodiment of the present invention will be described. In the second example embodiment, the feature amount used for stress estimation is different from that of the first example embodiment, but the other points are the same as those of the first example embodiment. Therefore, the same matter as that of the first example embodiment will not be described. In the first example embodiment, a ratio at which the first-order differential or the second-order differential of the awakening degree is smaller than the threshold value, i.e., "% (Δawakening degree<threshold value)" or "% (ΔΔ awakening degree<threshold value)" is used as the feature amount. In contrast, in the second example embodiment, a histogram of the values of the first-order differential or the second-order differential of the awakening degree is used as the feature amount.

Figure 10A:
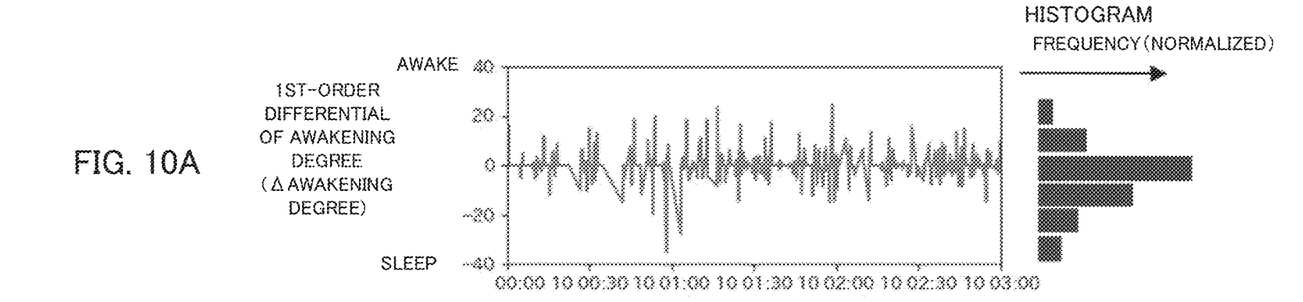
FIGS. 10A and 10B are diagrams for explaining a feature amount in a second example embodiment.
Figure 10B:
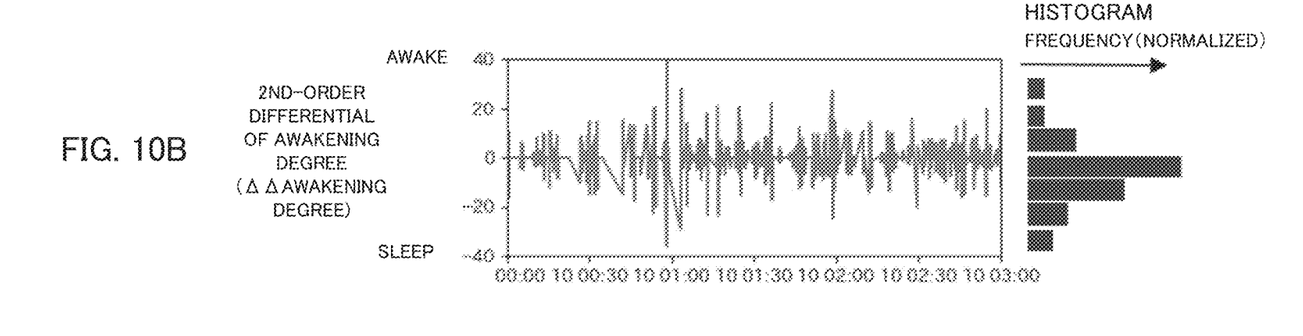

FIGS. 10A and 10B are diagrams for explaining a feature amount in the second example embodiment. FIG. 10A shows an example of generating a histogram based on the values of the first-order differential of the awakening degree, and FIG. 10B shows an example of generating a histogram based on the values of the second-order differential of the awakening degree. Incidentally, the frequency in the histogram is normalized. The width and number of the plurality of bins constituting the histogram are appropriately determined in advance. Incidentally, a known neural network for automatically adjusting the width and number of bins in the histogram may be used. In the second example embodiment, the information defining the histogram thus generated, specifically, the width and the number of bins, the frequency in each bin, the shape of the histogram itself, and the like are used as the feature amounts. Specifically, learning is performed using information defining the histogram as training data, and a stress model is generated in advance. Then, the stress estimation unit 23 uses the stress model generated in advance and estimates the stress from the feature amount calculated by the feature amount calculation unit 22, i.e., the information defining the histogram.

Third Example Embodiment

Figure 11:
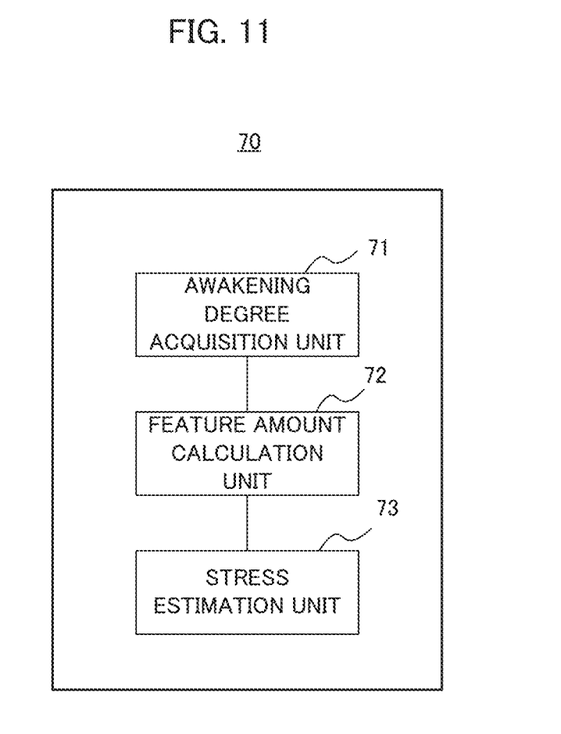
FIG. 11 shows a functional configuration of the stress estimation device according to a third example embodiment.

Next, a third example embodiment of the present invention will be described. FIG. 11 is a block diagram showing the functional configuration of the stress estimation device according to the third example embodiment. As illustrated, the stress estimation device 70 includes an awakening degree acquisition unit 71, a feature amount calculation unit 72, and a stress estimation unit 73. The awakening degree acquisition unit 71 acquires the awakening degree of the subject. Specifically, the awakening degree acquisition unit 71 may generate the awakening degree based on the captured image of the subject's face, or may simply receive the awakening degree generated by the external device. The feature amount calculation unit 72 calculates the feature amount of the acquired awakening degree. The feature amount of the awakening degree is the ratio at which the temporal change of the awakening degree is within a predetermined range, information which defines the histogram showing the distribution of the temporal change of the awakening degree, or the like. The stress estimation unit 73 estimates the stress from the calculated feature amount using a stress model prepared in advance.

[Modification]

While the stress estimation is performed using the awakening degree of the subject in the above-described example embodiments, an index indicating the sleepiness of the subject may be acquired or generated, and this may be used as the awakening degree. However, an index indicating sleepiness is often a value which increases when sleepiness is large and decreases when sleepiness is small. Therefore, in that case, a ratio at which the first-order differential or the second-order differential of the awakening degree (=drowsiness) is larger than a predetermined threshold value may be used as the feature amount.

While the present invention has been described with reference to the example embodiments and examples, the present invention is not limited to the above example embodiments and examples. Various changes which can be understood by those skilled in the art within the scope of the present invention can be made in the configuration and details of the present invention.

DESCRIPTION OF SYMBOLS 1, 70 Stress estimation device
2 Camera
12 Processor
13 Memory
14 Recording medium
21 Awakening degree generation unit
22 Feature amount calculation unit
23 Stress estimation unit
24 Stress model storage unit

What is claimed is:

1. A system comprising:
a camera configured to capture an image of a subject, the image including an eye of the subject;
a display device;
a memory storing instructions; and
one or more processors configured to execute the instructions to:
acquire the image of the subject captured by the camera;
detect an eye opening degree of the subject from the acquired image, the eye opening degree being a first time series signal;
determine an awakening degree of the subject based on the eye opening degree of the subject, the awakening degree being a second time series signal;
calculate a feature amount of the acquired awakening degree;
estimate stress from the calculated feature amount using a stress model;
determine whether the stress is greater than a threshold; and
display a message on the display device prompting the subject to take a rest when the stress has been determined to be greater than the threshold,
wherein the feature amount is a ratio at which a temporal change of the awakening degree is within a predetermined range, or information that defines a histogram indicating a distribution of the temporal change of the awakening degree, and
wherein the temporal change of the awakening degree is a first-order differential or a second-order differential of the awakening degree.

2. The system according to claim 1,
wherein the one or more processors acquire determine the awakening degree while the subject is awake.

3. The system according to claim 1,
wherein the stress model is generated in advance by performing training which uses the feature amount as training data and a stress value associated with the feature amount as a label.

4. A stress estimation method performed by a computer and comprising:
acquiring an image of a subject captured by a camera, the image including an eye of the subject;

detecting an eye opening degree of the subject from the acquired image, the eye opening degree being a first time series signal;

determining an awakening degree of the subject based on the eye opening degree of the subject, the awakening degree being a second time series signal;

calculating a feature amount of the acquired awakening degree;

estimating stress from the calculated feature amount using a stress model;

determining whether the stress is greater than a threshold; and displaying a message on a display device prompting the subject to take a rest when the stress has been determined to be greater than the threshold, wherein the feature amount is a ratio at which a temporal change of the awakening degree is within a predetermined range, or information that defines a histogram indicating a distribution of the temporal change of the awakening degree, and wherein the temporal change of the awakening degree is a first-order differential or a second-order differential of the awakening degree.

5. A non-transitory computer-readable recording medium storing a program executable by a computer to perform:

acquiring an image of a subject captured by a camera, the image including an eye of the subject;

detecting an eye opening degree of the subject from the acquired image, the eye opening degree being a first time series signal;

determining an awakening degree of the subject based on the eye opening degree of the subject, the awakening degree being a second time series signal;

calculating a feature amount of the acquired awakening degree;

estimating stress from the calculated feature amount using a stress model;

determining whether the stress is greater than a threshold; and displaying a message on a display device prompting the subject to take a rest when the stress has been determined to be greater than the threshold, wherein the feature amount is a ratio at which a temporal change of the awakening degree is within a predetermined range, or information that defines a histogram indicating a distribution of the temporal change of the awakening degree, and wherein the temporal change of the awakening degree is a first-order differential or a second-order differential of the awakening degree.

* * * * *